(12) United States Patent  
Raksi (10) Patent No.: US 9,770,362 B2  
(45) Date of Patent: Sep. 26, 2017

(54) WAVEFRONT CORRECTION FOR OPHTHALMIC SURGICAL LASERS

(71) Applicant: Novartis AG, Basel (CH)

(72) Inventor: Ferenc Raksi, Mission Viejo, CA (US)

(73) Assignee: NOVARTIS AG, Basel (CH)

( * ) Notice: Subject to any disclaimer, the term of this patent is extended or adjusted under 35 U.S.C. 154(b) by 155 days.

(21) Appl. No.: 14/581,236

(22) Filed: Dec. 23, 2014

(65) Prior Publication Data

US 2016/0175145 A1  Jun. 23, 2016

(51) Int. Cl.
| | |
|---|---|
| *A61F 9/00* | (2006.01) |
| *A61F 9/008* | (2006.01) |
| *A61B 3/10* | (2006.01) |
| *G02B 26/06* | (2006.01) |
| *A61B 18/20* | (2006.01) |

(52) U.S. Cl.
CPC ............ *A61F 9/008* (2013.01); *A61B 3/1015* (2013.01); *A61F 9/0084* (2013.01); *A61F 9/00825* (2013.01); *G02B 26/06* (2013.01); *A61B 2018/2005* (2013.01); *A61F 2009/0087* (2013.01); *A61F 2009/00848* (2013.01); *A61F 2009/00851* (2013.01); *A61F 2009/00872* (2013.01); *A61F 2009/00889* (2013.01); *A61F 2009/00897* (2013.01)

(58) Field of Classification Search
USPC .................................... 606/2–19; 607/88–94
See application file for complete search history.

(56) References Cited

U.S. PATENT DOCUMENTS

| | | | | |
|---|---|---|---|---|
| 5,521,705 A | * | 5/1996 | Oldenbourg | ....... G02B 21/0096 356/368 |
| 6,155,684 A | | 12/2000 | Bille et al. | |
| | | (Continued) | | |

FOREIGN PATENT DOCUMENTS

EP    1210923    6/2002

OTHER PUBLICATIONS

PCT International Search Report for corresponding International Application No. PCT/US2015/065008 dated Apr. 4, 2016, 5 pages.
PCT International Written Opinion for corresponding International Application No. PCT/US2015/065008 dated Apr. 4, 2016, 7 pages.

*Primary Examiner* — Lynsey Eiseman
*Assistant Examiner* — Dacheng Xie
(74) *Attorney, Agent, or Firm* — S. Brannon Latimer (57) ABSTRACT

A surgical laser system includes a laser engine, configured to generate a laser beam of laser pulses; a proximal optics and a distal optics, together configured to direct the laser beam to a target region, and to scan the laser beam in the target region through a scanning-point sequence; and an aberration sensor, configured to sense aberration by an aberration layer; a compensation controller, coupled to the aberration sensor, configured to generate compensation-point-dependent phase compensation control signals based on the sensed aberration; and a spatial phase compensator, positioned between the proximal optics and the distal optics, at a conjugate aberration surface, conjugate to the aberration layer, and coupled to the compensation controller, configured to receive the compensation-point-dependent phase compensation control signals, and to alter a phase of the laser beam in a compensation-point-dependent manner to compensate the sensed aberration.

19 Claims, 10 Drawing Sheets

(56) References Cited

U.S. PATENT DOCUMENTS

| | | | |
|---|---|---|---|
| 6,220,707 | B1 | 4/2001 | Bille |
| 6,688,745 | B2 | 2/2004 | Ross et al. |
| 6,746,121 | B2 | 6/2004 | Ross et al. |
| 6,827,442 | B2 | 12/2004 | Ross et al. |
| 6,887,232 | B2 | 5/2005 | Bille |
| 7,611,244 | B2 | 11/2009 | Bille |
| 7,988,295 | B2 | 8/2011 | Bille |
| 8,020,994 | B2 | 9/2011 | Bille |
| 8,403,484 | B2 | 3/2013 | Bille |
| 2002/0135733 | A1* | 9/2002 | Portney ............... A61F 2/1618 351/159.41 |
| 2009/0137990 | A1* | 5/2009 | Sheinis ............... A61F 9/008 606/5 |
| 2010/0103372 | A1* | 4/2010 | Bille ............... A61B 3/1225 351/205 |
| 2010/0173100 | A1* | 7/2010 | Weiss ............... B01J 3/006 427/582 |
| 2011/0028958 | A1* | 2/2011 | Raksi ............... A61F 9/008 606/6 |
| 2012/0044455 | A1* | 2/2012 | Hirose ............... G01B 11/2441 351/206 |
| 2012/0287400 | A1 | 11/2012 | Utagawa |
| 2013/0009156 | A1 | 1/2013 | Cho et al. |
| 2014/0216468 | A1* | 8/2014 | Goldshleger ........... A61F 9/009 128/845 |
| 2014/0257256 | A1* | 9/2014 | Hohla ............... A61F 9/008 606/4 |

* cited by examiner

WAVEFRONT CORRECTION FOR OPHTHALMIC SURGICAL LASERS

TECHNICAL FIELD

This patent document relates to surgical laser systems. More precisely, this patent document relates to correcting a laser beam wavefront by a spatial phase compensator in ophthalmic surgical laser systems.

BACKGROUND

Surgery with femtosecond ophthalmic lasers is based on generating a pulsed laser beam and delivering the laser pulses by a scanning delivery system through a focusing optics to a sequence of focus spots along a scan-pattern in a target region of an ophthalmic tissue. Each laser pulse creates a plasma or cavitation bubble in the target tissue at the focus spot of the laser beam when the beam intensity or energy density exceeds a plasma or photodisruption threshold. During surgery, the focus spot of the laser beam is scanned along a three dimensional scan-pattern, creating a sequence of these bubbles to form macroscopic surgical cuts or photodisrupted regions.

During the surgery, however, the laser beam can also cause unintended collateral damage away from the focus spot such as excessive heating and shockwaves in the target tissue and light poisoning in the retina. Therefore, surgical systems are designed to deliver the laser beam with an energy density that exceeds the photodisruption threshold, but only marginally to achieve the surgical functionality while minimizing the collateral damage.

The energy density or beam intensity is determined by the energy, duration and repetition rate of the individual laser pulses and the size of the focus spot. Modern surgical laser systems provide high precision and control by using precisely controlled laser sources, refined optical designs, high quality optical parts and an objective with a large numerical aperture to focus the laser beam down to a diffraction limited focus spot with a diameter of a few microns, and do so at all points of the scan-pattern within a surgical volume, or at all scanner positions of the surgical laser system. This high precision makes the modern laser surgical systems capable of maintaining the beam intensity marginally above the plasma threshold along the entire scan-pattern within the surgical volume in ideal or model targets.

Unfortunately, in spite of all the design and manufacturing effort spent on optimizing the laser sources and optics, the focus spot in the ophthalmic target region is often still larger than its diffraction limited value because the target tissue itself often gets distorted, making it different from the ideal or model targets used during the design of the laser optics. Distortions can be also caused by imperfections of the scanning delivery system and the focusing optics. The enlarging of the focus spot caused by any of these distortions can lead to failing surgical performance since it lowers the pulse energy density or beam intensity below the plasma threshold and thus prevents the scanning laser beam from forming the planned surgical cuts, leaving uncut lines or regions in the target region.

This problem of failing surgical performance can become particularly acute during surgical cuts where the targeted tissue is very thin such as a capsulotomy of the thin lens capsular bag during a cataract surgery. Since the targeted tissue is thin, the laser beam scans it only once or only a few times along a loop, as this scan-pattern should be already capable of cutting through the entire thickness of the capsular bag. However, if any one of the above distortions reduces the beam intensity below the plasma threshold along a section of the loop then that section can remain uncut. This uncut section of the capsular bag needs to be cut and separated manually, possibly leading to a tearing of the capsular bag and thus to a substantial lowering of the precision of the cataract surgery.

Therefore, there is a need for surgical laser systems that can deliver the laser beam with a pulse energy density that is marginally higher than the plasma threshold in the entire surgical volume even if distortions are present along the beam path either in the target region or in the optical system itself, as such laser systems are capable of cutting the target region according to the scan-pattern in the entire surgical volume without leaving uncut regions or lines.

SUMMARY

Figure 1A:
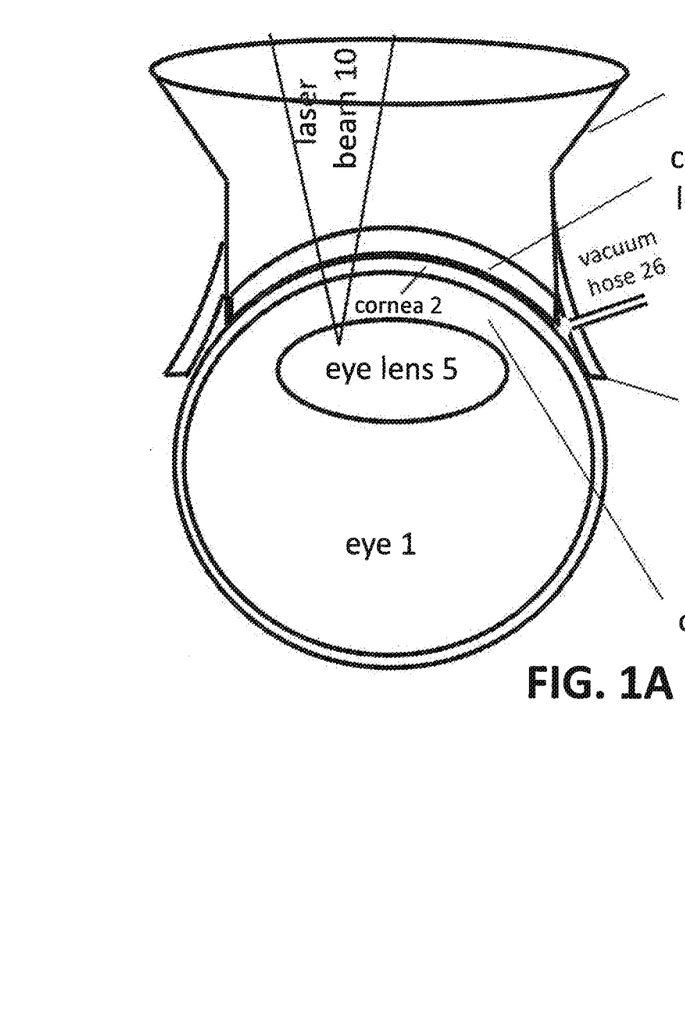
FIGS. 1A-E illustrate an effect of a wrinkled cornea on an ophthalmic surgical laser beam.

FIG. 1A illustrates that an objective of cataract surgery is to direct or deliver a surgical laser beam 10 into an eye 1 through its cornea 2 and anterior chamber 3 to photodisrupt a cataractous target region in a lens 5. FIGS. 1A-E illustrate some of the problems caused by beam distortions in cataract surgery. FIG. 1A illustrates that many surgical laser systems have a patient interface (PI) 20 attached to a distal end of an objective of the laser scanning delivery system. The PI 20 can include a contact lens 22 that makes contact with the cornea 2 to allow a well-controlled entry of the surgical laser beam 10 into the cornea 2. The PI 20 is often outfitted with a suction ring 24 and a vacuum hose 26 for creating a reliable mechanical coupling with the eye 1.

Figure 1B:
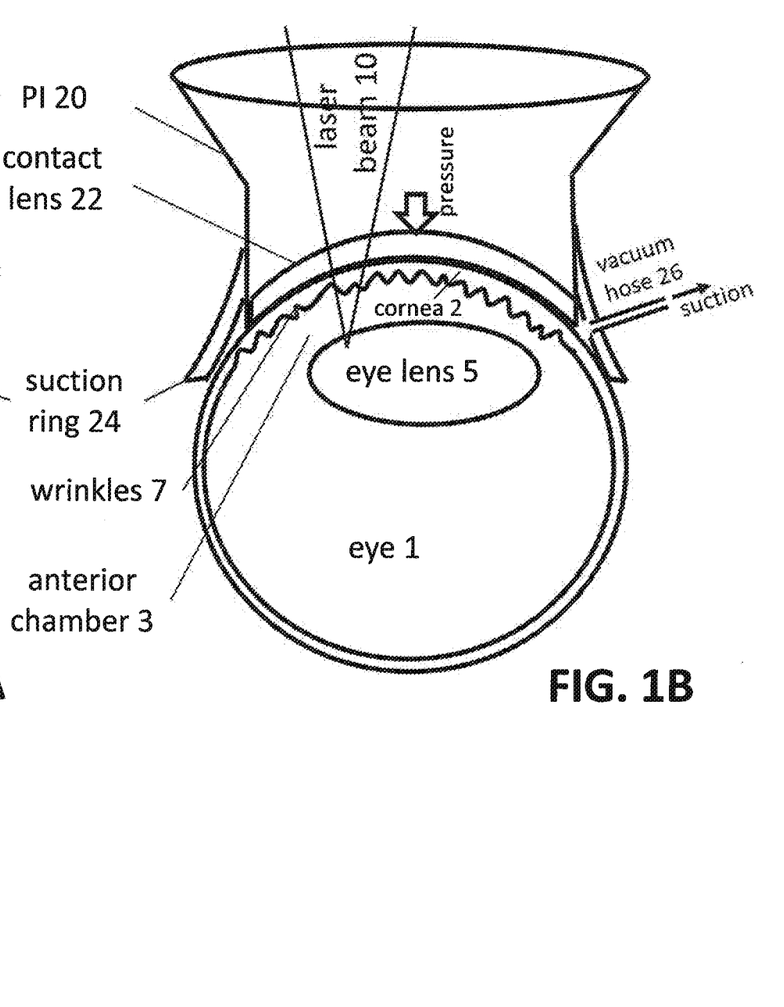

FIG. 1B illustrates that the PI 20 and its contact lens 22 can be coupled to the cornea 2 reliably by applying suction to the vacuum hose 26 that presses the contact lens 22 to the cornea 2. Sometimes, the PI 20 and its contact lens 22 can be additionally pressed against the cornea 2 by its own weight or by a mechanical system such as spring loading.

FIG. 1B also shows that, unfortunately, the pressure caused by the vacuum suction and the mechanical pressure can create wrinkles 7 in the cornea 2 which can cause the above mentioned beam distortions.

Figure 1C:
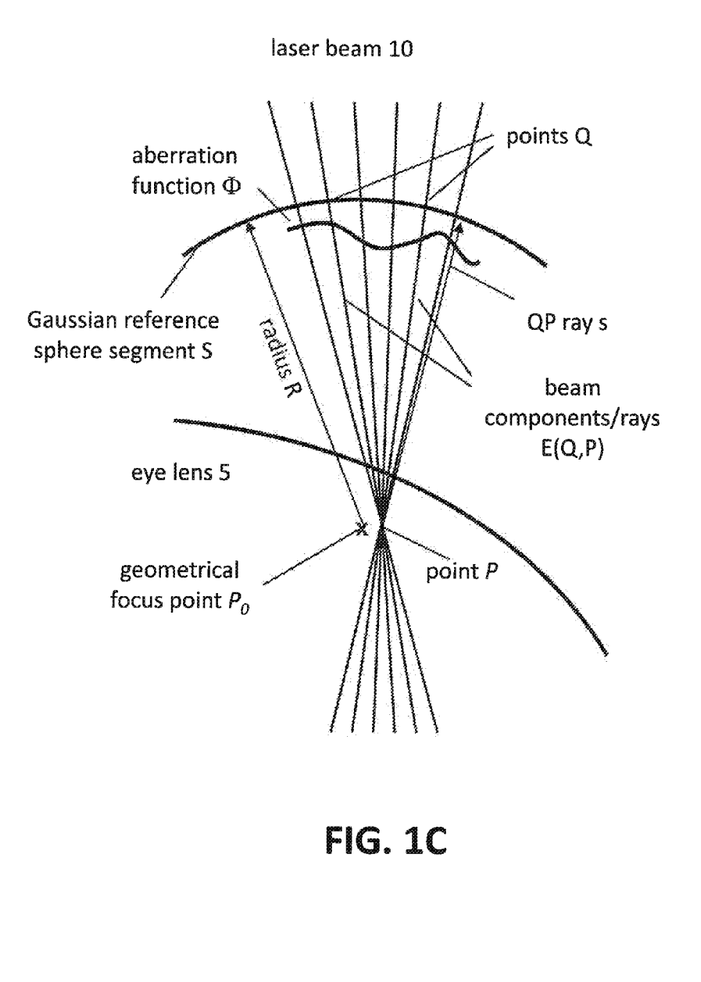

FIG. 1C illustrates a mathematical formulation of the distortions or aberrations of the laser beam 10. It is customary to define an aberration as the deviation of a wavefront of the laser beam 10 from a conceptual Gaussian reference sphere segment S of radius R. The Gaussian sphere segment S can be centered on the geometrical focal point $P_0$ of the laser beam 10 and formed by the intersection of the laser beam 10 and an entire Gaussian reference sphere. In many cases, the reference sphere segment S is the pupil of the laser system. The two main classes of distortions or aberrations are phase and amplitude distortions/aberrations. The formulation is presented here for the more typical phase aberrations. Amplitude aberrations can be described in an analogous manner.

It is known from the theory of optical wave propagation that the intensity of light I(P) at a point P in the focal plane that contains the geometrical focus point $P_0$ is given by the absolute value squared of the electromagnetic disturbance, in essence the electric field, with the fast oscillating $e^{i\omega t}$ factor removed:

$$I(P) = |U(P)|^2.$$

According to the Huygens-Fresnel principle, the electric field U(P) at the point P is given by an integral of the beam components, or rays, E(Q,P) over the Gaussian reference sphere segment S:

$$U(P) = -\frac{i}{\lambda} \int \int_S E(Q, P) dS(Q)$$

$$= -\frac{i}{\lambda} \int \int_S E_0(Q, P) e^{ik\Phi} dS(Q)$$

$$= -\frac{i}{\lambda} \int \int_S A \frac{e^{ik(s-R)} e^{ik\Phi}}{sR} dS(Q)$$

Here, E(Q,P) is the propagating electric field, beam component or ray that propagates from a dS(Q) vicinity of point Q on the Gaussian reference sphere segment S to the point P of the focal plane near $P_0$, the geometrical focus point. This beam component can be decomposed into $E_0$(Q,P), the propagating electric field in the absence of a phase aberration and into $e^{ik\Phi}$, representing the phase aberration by a phase aberration function $\Phi$. The undistorted field can be represented as:

$$E_0(Q, P) = A \frac{e^{ik(s-R)}}{Rs}.$$

Here, A is the amplitude of the beam component or ray at point Q, reduced during the propagation to point P by 1/s, where s is the length of the QP ray from the point Q to point P. Further, $e^{ik(s-R)}$ represents the propagating wave phase factor, acquired by the propagating electromagnetic wave $E_0$(Q,P) in the absence of aberrations. Finally, $k=2\pi/\lambda$ is the wavenumber and $\lambda$ is the wavelength of the laser beam 10. Discussing the aberration-free beam, for $P=P_0$ s=R and thus the phase factors of the beam components that propagate from the different Q points of the reference sphere segment S to the geometrical focus point $P_0$ add up with maximum constructive interference. Further, as known, the interference remains constructive in a small but finite vicinity of the geometrical focus point $P_0$, broadening the geometrical focus point $P_0$ into a diffraction limited focus spot 32.

Figure 1D:
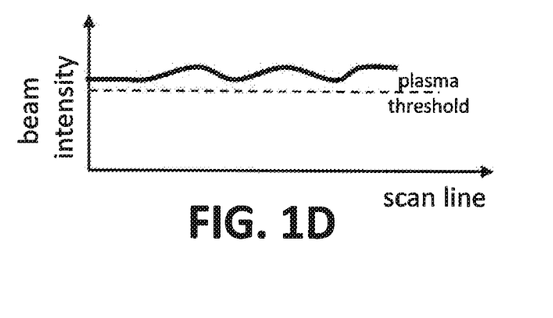

FIG. 1D illustrates the beam intensity along a typical scan line in the target region when the laser beam is scanned over an unwrinkled cornea. Since the aberration function is essentially zero in this region, the propagating wave phase factors $e^{ik(s-R)}$ of the beam components E(Q,P) in the Huygens-Fresnel integral can add smoothly and constructively when reaching P points in the vicinity the geometrical focus point $P_0$, thus producing a laser beam 10 with a beam intensity that can remain above the plasma threshold along the shown and the other scan lines within the surgical volume. Therefore, as the laser beam 10 is scanned across the scan lines of the scan-pattern, it can create the intended surgical cuts in the entire surgical volume.

Figure 1E:
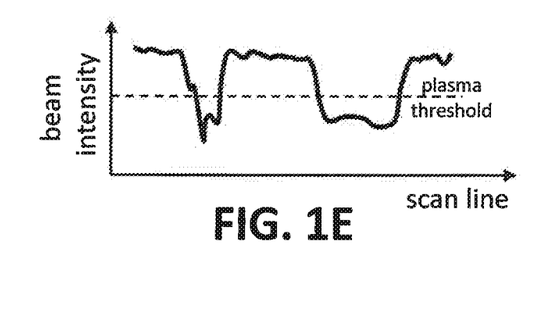

FIG. 1E illustrates that, in contrast to the unwrinkled case of FIG. 1D, if the vacuum suction or the mechanical pressure creates corneal wrinkles 7, then these wrinkles 7 can distort the laser beam 10 by refracting the propagating electric fields, or beam components, to distorted directions, so that their aberration function $\Phi$ in the Huygens-Fresnel integral become different from zero. The corresponding phase factors $e^{ik\Phi}$ can lead to a substantially destructive interference between the beam components, possibly substantially reducing the beam intensity. The magnitude of the corneal phase aberration can be estimated as the product of the amplitude of the wrinkles and the change of the refractive index at the cornea-aqueous humor interface. The refractive index of the cornea is approximately 1.377 while the index of the aqueous humor is 1.337, separated by a difference of 0.04. As an example, for a laser wavelength of 1 micrometer, wrinkles with amplitude of 25 micrometers give approximately $2\pi$ phase aberration. Therefore, in general, for $\Phi > \pi/4$ the phase aberrations can already substantially reduce the beam intensity, and for $\Phi > \pi/2$ the aberrations even reverse the sign of the contributions of the beam components E(Q,P) to the Huygens-Fresnel integral. These destructive interferences can reduce the beam intensity at the focus spot 32 to a value below the plasma threshold and thus preventing the laser beam 10 from photodisrupting the target region and from executing the surgical cuts along the surgical scan-pattern, instead leaving uncut regions behind. In some cases, the single focus spot may even break up into multiple foci.

Figure 2A:
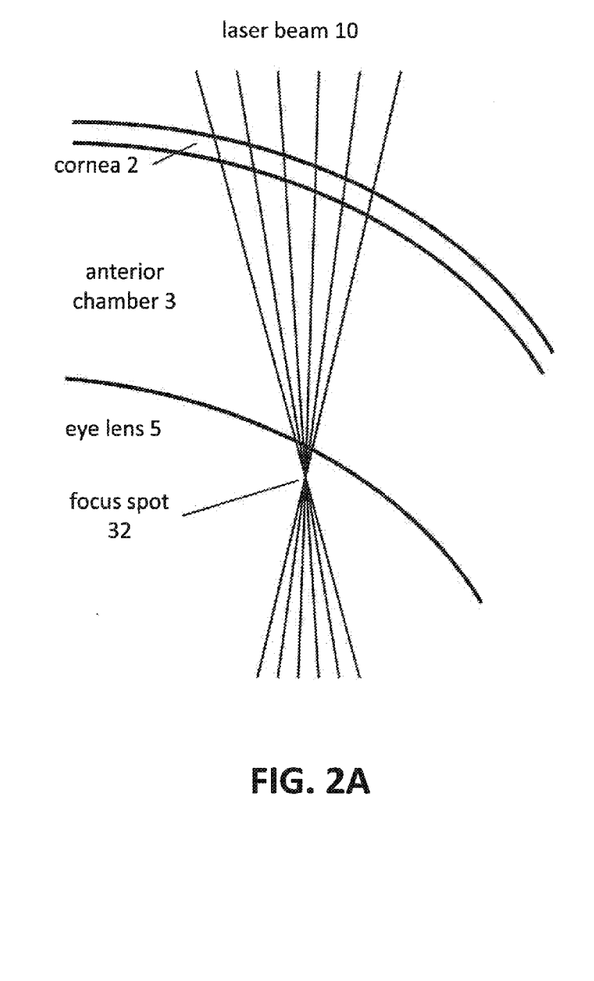
FIGS. 2A-C illustrate an enlargement of a focus spot because of corneal wrinkling.
Figure 2B:
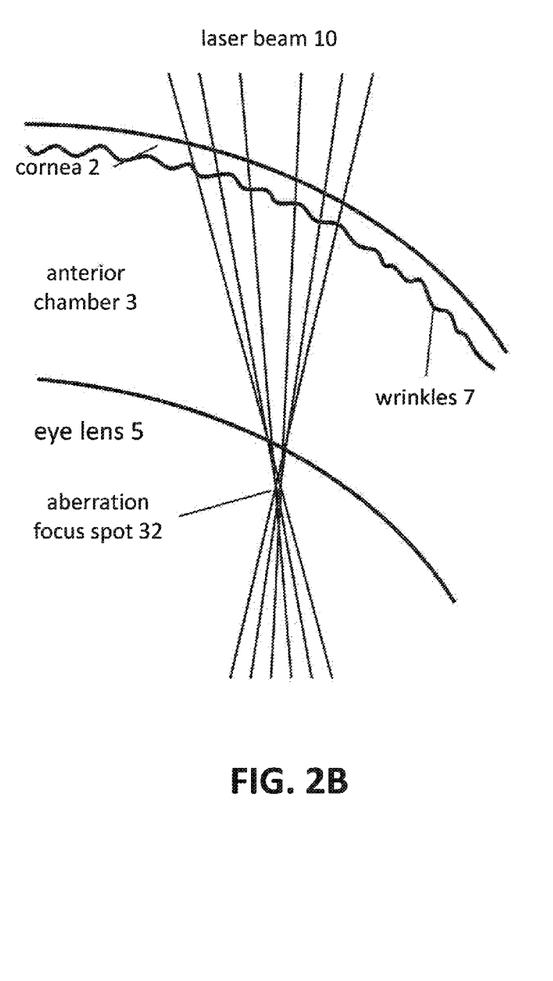

FIGS. 2A-B illustrate a related effect of corneal wrinkling. FIG. 2A illustrates that in the absence of corneal wrinkling the focus spot 32 of the laser beam 10 can have a near diffraction limited size of a few microns for a laser beam 10 with wavelength in the 500-1,500 nm range. The scanning delivery system and optics can be designed to deliver the laser beam 10 with an intensity to this focus spot 32 that marginally exceeds the plasma or photodisruption threshold everywhere in the surgical volume and thus is capable of executing the surgical cuts without leaving uncut regions behind.

FIG. 2B illustrates that when the vacuum suction or pressure of the PI 20 creates wrinkles 7 in the cornea 2, then the wrinkles 7 can redirect and refract some beam components to go through the plane of the focus spot 32, or focal plane, of the unwrinkled case smeared over an enlarged aberration focus spot 32. The increase of the focus spot area decreases the beam intensity, possibly below the plasma threshold. Besides causing destructive interference of the phase factors of the beam components, this focus-spot-smearing is an additional mechanism by which corneal wrinkling can reduce the beam intensity below the plasma threshold.

Figure 2C:
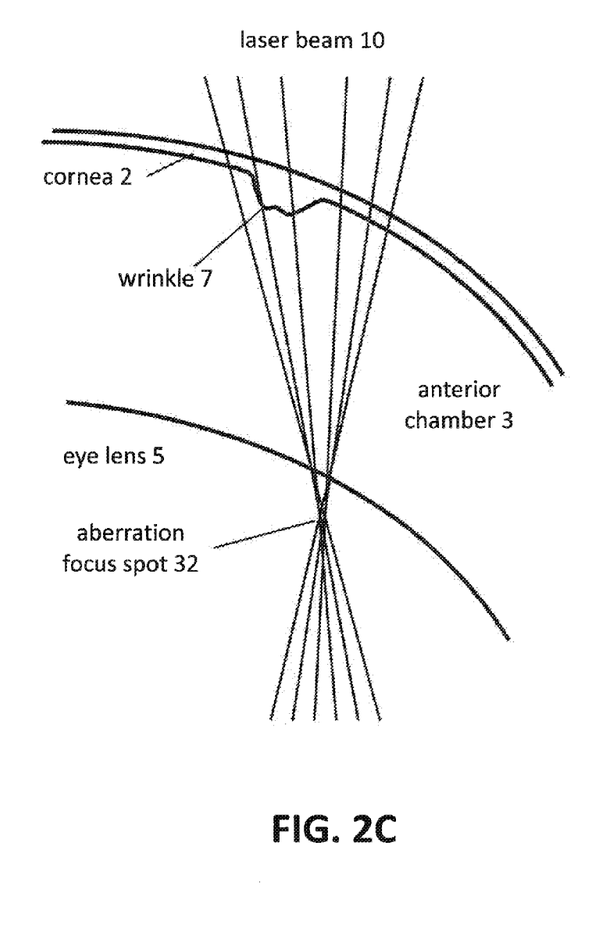

Finally, FIG. 2C illustrates a specific case of the problem in FIG. 2B: the formation of a single localized defect or wrinkle 7, created by the vacuum suction or the pressure of the PI 20. As before, the localized defect or wrinkle 7 can redirect or refract the laser beam 10 so that when the laser beam 10 goes through the focal plane, its beam components are smeared out over the enlarged aberration focus spot 32. As before, the increase of the focus spot area decreases the beam intensity, possibly reducing it below the plasma threshold.

Figure 3A:
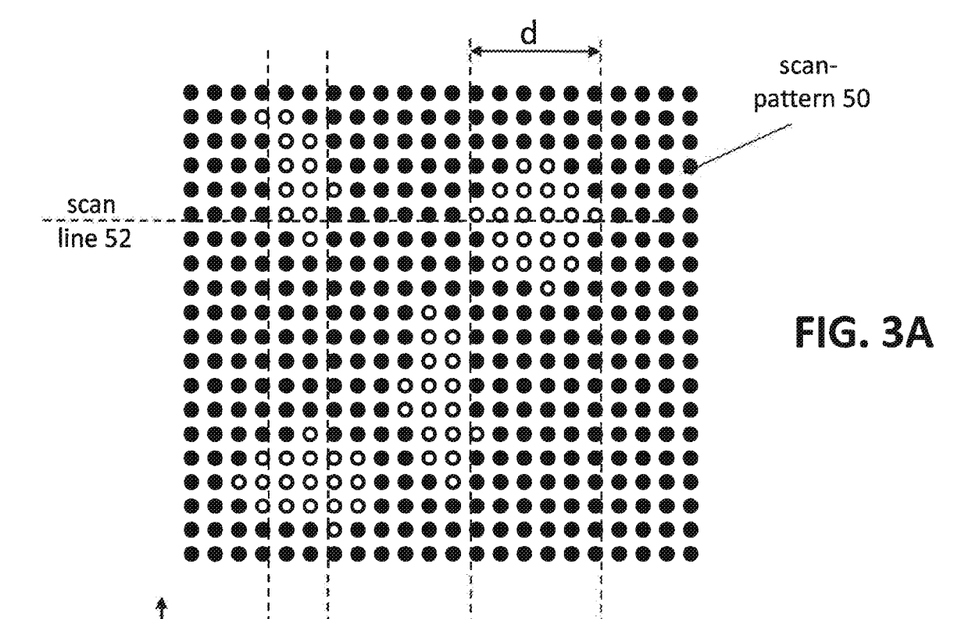
FIGS. 3A-B illustrate an effect of corneal wrinkling on a two dimensional cut.
Figure 3B:
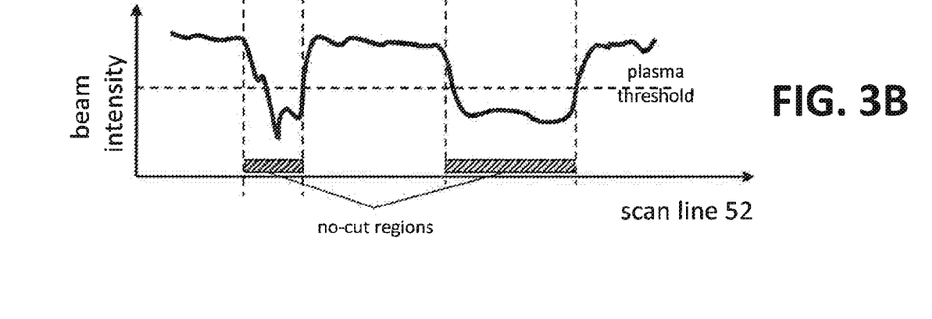

FIGS. 3A-B illustrate the analogous problem for a two dimensional (2D) scan-pattern 50. Such a 2D scan-pattern 50 can be used when an ophthalmic layer is to be cut, or a volume is to be photodisrupted. The laser beam 10 can be scanned along the 2D scan-pattern to create a densely packed layer of photodisrupted bubbles. This photodisrupted layer can effectively cut apart the tissue segments on its two sides. However, if the laser beam 10 is distorted by a wrinkled cornea, at several of the intended spots of the scan-pattern 50 the beam intensity may be reduced below the plasma threshold, and thus the laser beam 10 may fail to create the photodisrupted bubbles, as shown in FIG. 3A.

FIG. 3B illustrates that the beam intensity may be reduced below the plasma threshold for extended "no-cut regions" or "uncut regions" of the size d along a typical scan line 52, where d can be comparable to the size of the corneal wrinkles 7. In typical ophthalmic cases, d can vary from about 10 microns to beyond 1 millimeter. Referring back to FIG. 3A, these uncut regions can have a spatial extent beyond a millimeter in one, two or even all three dimensions. Therefore, when the scanning of the laser beam 10 is finished, the intended surgical cuts will be interrupted by extended no-cut regions.

The surgeon may attempt to cut these no-cut regions by re-scanning the entire scan pattern or portions of the scan-pattern 50. However, this is not very effective, since the same wrinkles are still present in the cornea, giving rise to the same aberrations. Thus, the same regions will remain uncut during the second scan. Re-scanning is also time-consuming. Every time the surgeon is forced to repeat a surgical step, valuable surgical time is spent, increasing the probability of undesirable outcomes.

Therefore, the surgeon may be forced to cut the uncut regions manually to complete the surgery, possibly creating jagged edges, leading to the formation of tears in the ophthalmic tissue. These undesirable effects call out for improvements in the surgical laser systems that reduce or eliminate the formation of the uncut regions.

Briefly and generally, embodiments of the invention offer solutions to the above problems by providing a surgical laser system, comprising: a laser engine, configured to generate a laser beam of laser pulses; a proximal optics and a distal optics, together configured to direct the laser beam to a target region, and to scan the laser beam in the target region through a scanning-point sequence; and an aberration sensor, configured to sense aberration by an aberration layer; a compensation controller, coupled to the aberration sensor, configured to generate compensation-point-dependent phase compensation control signals based on the sensed aberration; and a spatial phase compensator, positioned between the proximal optics and the distal optics, at a conjugate aberration surface, conjugate to the aberration layer, and coupled to the compensation controller, configured to receive the compensation-point-dependent phase compensation control signals, and to alter a phase of the laser beam in a compensation-point-dependent manner to compensate the sensed aberration.

In some embodiments, a method of reducing aberrations in a surgical laser system comprises: generating a laser beam of laser pulses by a laser engine; directing the laser beam to a target region by a proximal optics and a distal optics; scanning the laser beam in the target region by the proximal optics and the distal optics through a scanning-point sequence; sensing aberration, caused by an aberration layer, with an aberration sensor; generating compensation-point-dependent phase compensation control signals based on the sensed aberration by a compensation controller, coupled to the aberration sensor; and altering a phase of the laser beam in a compensation-point-dependent manner to compensate the sensed aberration by a spatial phase compensator, positioned between the proximal optics and the distal optics, at a conjugate aberration surface, conjugate to the aberration layer, and coupled to the compensation controller to receive the compensation-point-dependent phase compensation control signals.

DETAILED DESCRIPTION

Methods are known to manipulate or correct a distorted waveform or wavefront of light to counteract the effect of distortions due to the optics, the medium or the target, as this problem arises from medicine to astronomy, where the atmospheric distortions need to be compensated. However, correcting the distorted wavefront with a phase modulator remains a difficult challenge for multiple reasons.

First, such systems need to have a suitable wavefront analyzer and associated optics. Such analyzers are expensive, increase the complexity and the size of the system and are often cumbersome to use.

Second, even if a wavefront analyzer is implemented, the distorted wavefront reaching the ocular target, such as the lens of the eye, is not available for analysis, as a substantial portion of the distortion can occur after the beam left the optical system. For example, the earlier described wrinkling of the cornea can distort the laser beam to a substantial degree after the beam exited the optical system and entered the eye. Some systems attempt to capture this additional distortion by analyzing the beam reflected from the retina. However, the beam reflected from the retina potentially picks up additional distortions from ocular regions past the target such as the lens, and it gets distorted twice, on its way in and out of the eye. Also, more advanced cataracts, such as class 4 cataracts, may largely absorb the reflected beam.

Third, the detection and analysis of the distorted wavefront needs to be processed to determine the phase modulation response needed to correct the distorted wavefront. This determined response then needs to be coupled back to an aberration controller by a feedback control loop. These requirements are particularly demanding to implement in a scanning system like an ophthalmic surgical laser. The detection, analysis, processing and feeding back all need to be done in real time during scanning Doing so requires substantial signal processing bandwidth and advanced electronics.

Fourth, the requirement of real-time phase modulation is particularly pressing in a modern, high speed XYZ scanning ophthalmic surgical system, where the repetition rate of the pulsed laser beam can be 50 kHz or even 150 kHz. As the beam is scanned through target points with different XYZ coordinates in a target volume, its distortion continues to change, caused by centers throughout the target volume. Accordingly, the phase modulation response needs to be continuously detected, re-analyzed and re-processed, and the re-processed phase modulation response has to be continuously fed back to the phase modulator. The high scanning speed of the ophthalmic surgical lasers places strong demands on the processing speed and signal bandwidth of all components of the system, the wavefront detector, analyzer, processor, and the phase modulator.

To address the above described problem of corneal wrinkling distorting the surgical laser beam, causing no-cut regions in a way different from the existing wavefront modulators, this patent document describes embodiments of a surgical laser system with a spatial phase modulator.

Embodiments of the surgical laser system are developed from the following considerations.

(1) The distortion of the laser beam in these ophthalmic systems is caused not by a volumetric distortion, but by a layer, the wrinkled distal boundary of the cornea. This will be referred to as the aberration layer.

(2) According to general principles of optical design, for imaging optics that create real images, an object layer or surface is imaged to a conjugate or image surface. This means that all the rays that go through a particular aberration point $r_a$ of the aberration layer also go through a corresponding conjugate, or compensation point $r_c$ on its conjugate surface. Since the location of the aberration layer relative to the optics is known to a substantial precision, the conjugate surface of this aberration layer inside the optics is known as well. Even in an optical system where the target's own conjugate surface is at infinity, the optical system can be designed such that the conjugate surface of the aberration layer is at a finite distance from the aberration surface, inside the optical system itself.

(3) At any given moment, the optics of a surgical laser focuses the rays of a typically expanded laser beam to a specific scanning point $r_s$ in the target region. Since typically the aberration layer is proximal to the target region, the rays that intersect each other in the target region in the specific scanning point $r_s$ intersect the aberration layer at aberration points $r_a$ that cover an extended area. Correspondingly, rays that go through the same aberration point $r_a$ are directed to different scanning points $r_s$. Since the aberration at the aberration point $r_a$ only depends on the source of aberration (e.g. a corneal wrinkle) specifically at $r_a$, the aberrations can be compensated by an $r_a$-dependent compensation which can be largely independent of the scanning point $r_s$.

(4) Because of the strong correspondence and mapping between the aberration points $r_a$ and the conjugate compensation points $r_c$, the aberrations at $r_a$ can be compensated by placing a spatial phase compensator at the conjugate surface. The spatial phase compensator can alter the phase of the rays at the compensation point $r_c$ that corresponds to the aberration point $r_a$ by an amount that compensates the aberration caused by the aberration layer at $r_a$.

Combining (3) and (4) illustrates that it is possible to compensate the aberrations caused by an aberration layer to rays directed to scanning points $r_s$ by positioning a spatial phase compensator at the conjugate surface of the aberration layer, and configuring the spatial phase compensator to introduce phase shifts that depend on the compensation points $r_c$, but not on the scanning points $r_s$.

(5) Typically the conjugate surface of the curved distal corneal boundary is curved. It is challenging to fabricate a phase modulator that is positioned at such a curved conjugate surface. However, embodiments have been developed from the recognition that it is possible to design an optical system where the conjugate surface of an aberration surface with a cornea-like curvature is essentially flat.

(6) Since the aberrations are dominantly caused by corneal wrinkling at the known location of the distal boundary of the cornea, it is possible to calculate the aberration optical path length from the knowledge of the shape and location of the wrinkles alone. This information can be gleaned from an optical coherence tomographic (OCT) image, without using a wavefront aberrometer. And since many ophthalmic laser systems already include an OCT imaging system, the aberration optical path can be determined without the need to insert additional and costly wavefront aberrometers.

Embodiments implement one or more of the above design considerations as follows.

Figure 4:
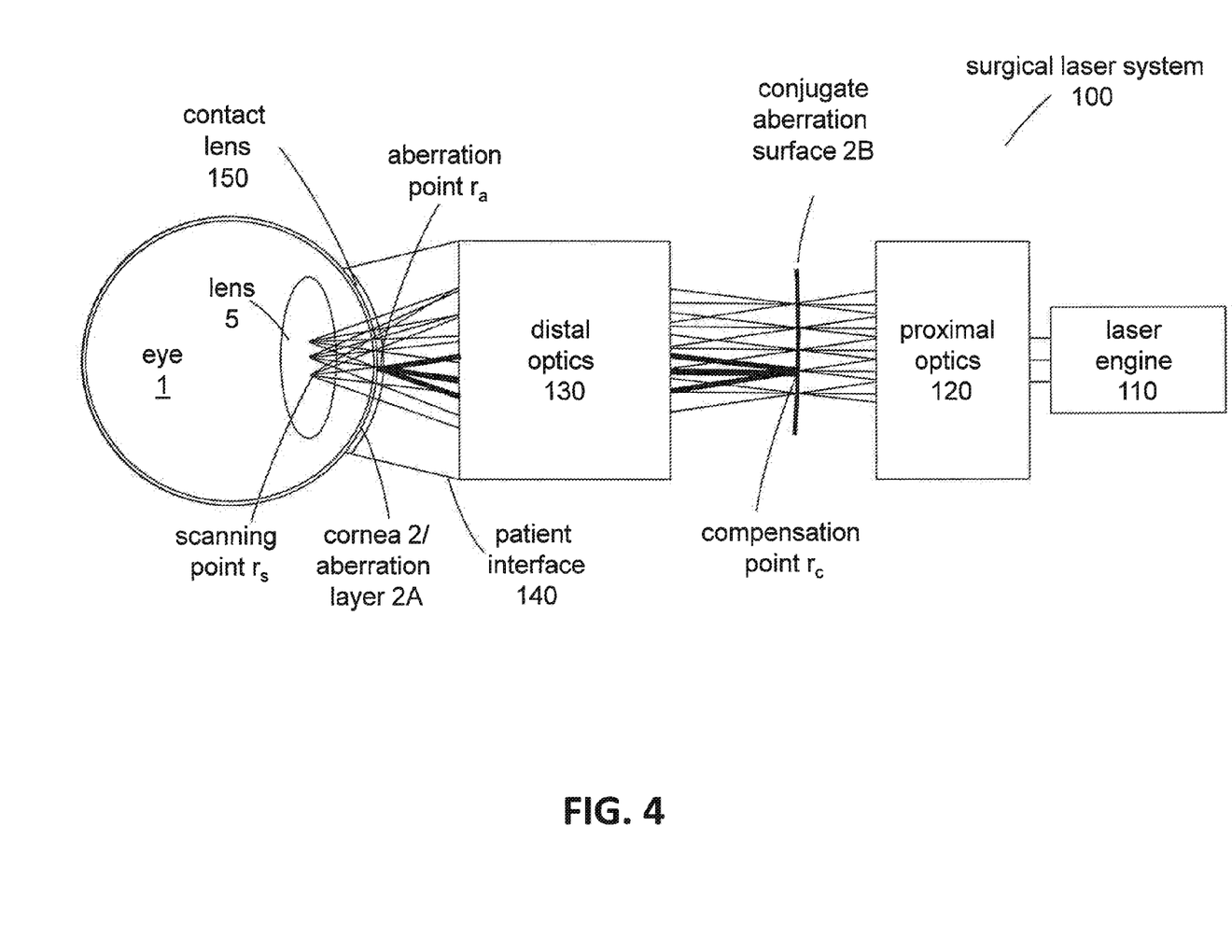
FIG. 4 illustrates an ophthalmic surgical laser system and its aberration layer.
Figure 5:
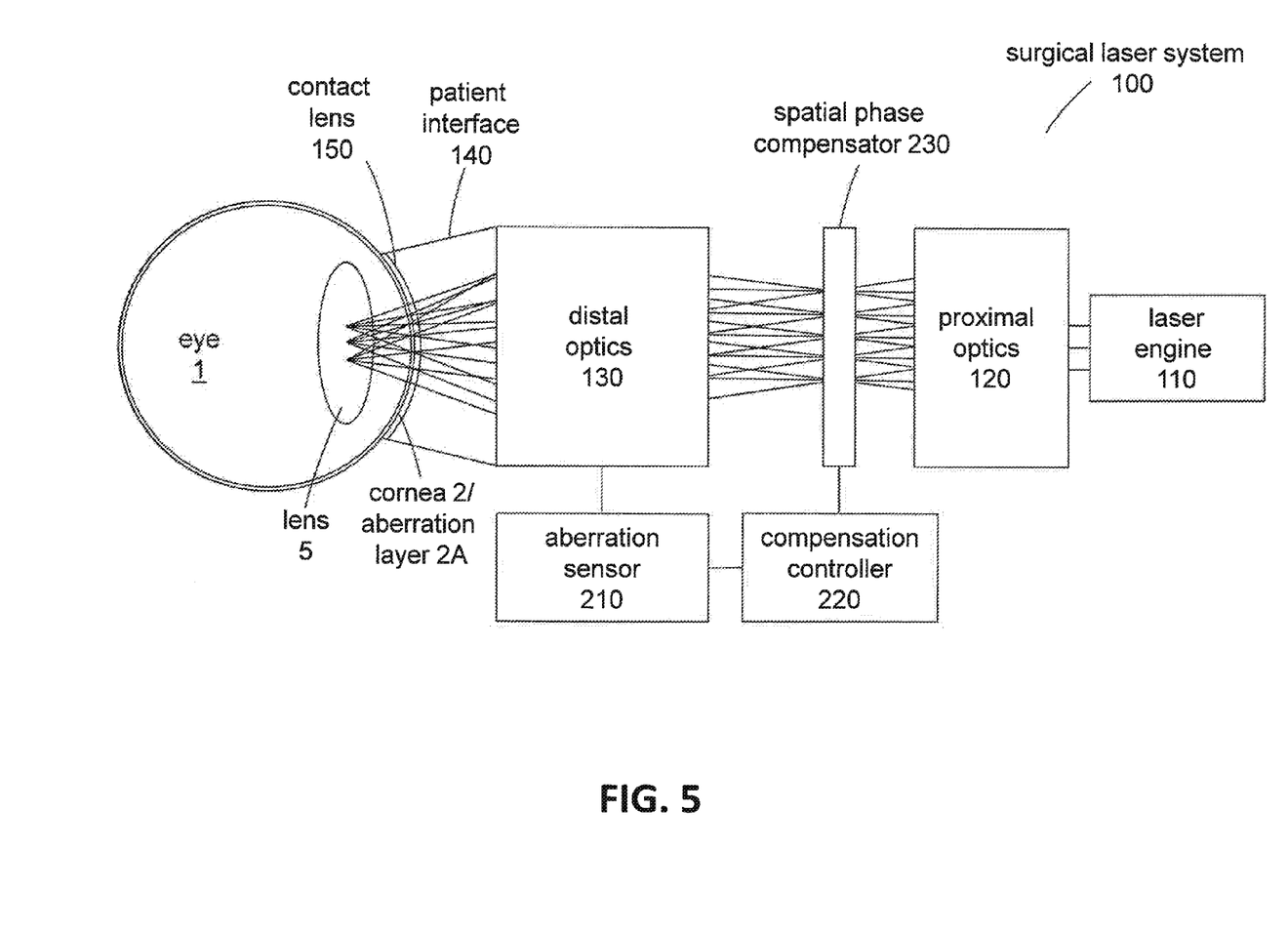
FIG. 5 illustrates an ophthalmic surgical laser system with a spatial phase compensator.

FIGS. 4-5 illustrate a surgical laser system 100 that can include a laser engine 110, configured to generate a laser beam of laser pulses; a proximal optics 120 and a distal optics 130, together configured to direct the laser beam to a target region, and to focus and scan the laser beam in the target region through a sequence of scanning points $r_s$. The distal optics 130 can also include a patient interface 140 with a contact lens 150 that makes contact with the cornea 2. As discussed above, in ophthalmic embodiments where the corneal wrinkling is a major source of the beam aberration, the aberration layer can be the distal boundary of the cornea 2, interfacing with the anterior chamber of the eye 1. In what follows, the general notion of the aberration layer is denoted by 2A, a specific example being the distal boundary of a wrinkled cornea 2. In these and other embodiments, the aberration layer 2A can have a fixed and known relationship with the contact lens 150 and therefore with the distal optics 130. For example, given that the average thickness of cornea 2 is in the range of 0.4 mm-0.8 mm, the aberration layer 2A can track a distal surface of the contact lens 150 at a distance between 0.1 mm-1 mm. The points of the aberration layer 2A are denoted by $r_a$.

As discussed before, FIG. 4 also illustrates that the aberration layer 2A has a conjugate aberration surface 2B whose points are denoted by $r_c$. By construction, the rays that go through a particular aberration point $r_a$ of the aberration layer 2A all intersect each other at the compensation point $r_c$ at the conjugate aberration surface 2B that corresponds to, or can be mapped to, the aberration point $r_a$. This is indicated for a specific aberration point $r_a$—compensation point $r_c$ pair by the thick solid lines in FIG. 4. The above recognitions (1)-(2), that for layer-like aberration sources like the aberration layer 2A such conjugate surfaces 2B exist, or the optical system can be designed such that they exist, are part of the platform on which the aberration-compensating embodiments of the surgical laser system 100 are developed.

It is recapped here for clarity that the optics 120-130 expands and then focuses the rays, or beam components, of the laser beam to a specific scanning point $r_s$ in the target region, such as the lens 5. Since typically the aberration layer 2A, such as the cornea 2, is proximal to the target region or lens 5, the rays that intersect each other in the target region at the specific scanning point $r_s$ go through the aberration layer at aberration points $r_a$ that cover an extended area. Correspondingly, rays that go through the same aberration point $r_a$ are directed to different scanning points $r_s$. Since the aberration at the aberration point $r_a$ only depends on the source of aberration specifically at $r_a$ (e.g. a corneal wrinkle), the aberrations can be compensated by an $r_a$-dependent compensation which can be largely independent of the scanning point $r_s$. Finally, there is a strong correspondence, or mapping, between the aberration points $r_a$ and the conjugate compensation points $r_c = r_c(r_a)$. Therefore, it is possible to compensate the aberrations caused by the aberration layer 2A at points $r_a$ during scanning the laser beam through a sequence of scanning points $r_s$ by altering the phase of the rays at the conjugate compensation points $r_c = r_c(r_a)$ of the conjugate aberration surface 2B that correspond to the aberrations points $r_a$, but are largely independent from the scanning points $r_s$. Here, in general the scanning points $r_s$, the aberration points $r_a$ and the compensation points $r_c$ all represent three dimensional vectors: $r_s = (x_s, y_s, z_s)$, $r_a = (x_a, y_a, z_a)$, and $r_c = (x_c, y_c, z_c)$.

It is noted here that during a typical cataract procedure the laser beam is focused into a lens target region that is distal to the corneal aberration layer 2A. There are some procedures where the target of the surgery is the cornea and thus the target region and the aberration layer can be quite close.

In such cases the distinction that the aberration compensation is $r_a/r_c$ dependent but $r_s$ independent may appear hollow. However, it is recalled that the aberrations are caused by the corneal wrinkles at the distal boundary of the cornea, distal to the surgical target region. Accordingly, the corneal wrinkles do not introduce substantial aberration for corneal surgical procedures.

It is further noted that even if the optics of the surgical laser system 100 is such that the image or conjugate surface of the surgical target is at infinity, corresponding to a parallel laser beam, the optics can be designed such that the conjugate aberration surface 2B of the aberration layer 2A can be inside the optics.

FIG. 5 illustrates that the surgical laser system 100 can further include an aberration sensor 210, configured to sense an aberration by the aberration layer 2A, and a compensation controller 220 that is coupled to the aberration sensor 210 to generate compensation-point-dependent phase compensation control signals based on the sensed aberration. The surgical laser system 100 can also include a spatial phase compensator 230 that is positioned between the proximal optics 120 and the distal optics 130, at the conjugate aberration surface 2B that is conjugate to the aberration layer 2A. The spatial phase compensator 230 can be coupled to the compensation controller 220 to receive the compensation-point-dependent phase compensation control signals and to alter a phase of the laser beam in a compensation-point-dependent manner to compensate the sensed aberration, sensed by the aberration sensor 210.

Placing the spatial phase compensator 230 at the conjugate aberration surface 2B makes it possible to introduce compensating phases at $r_c$ compensation points that are needed to compensate the aberration caused at the $r_a$ aberration points by, e.g., a corneal wrinkle of the aberration layer 2A, wherein the $r_c$ compensation points are the conjugates of the $r_a$ aberration points: $r_c=r_c(r_a)$.

As discussed above at (3)-(4), with this design the compensating phases are dependent from the $r_c$ compensation points, but can be essentially independent from the $r_s$ scanning points. Therefore, in some embodiments the compensation controller 220 can be a separate or independent subsystem from a scanner control subsystem. In some cases these two systems may use separate computer processors.

In embodiments of the surgical laser system 100 at least one of the proximal optics 120 and the distal optics 130 can be designed so that the conjugate aberration surface 2B is essentially flat. As discussed above at (5), systems with a flat conjugate aberration surface 2B are better suited to have a spatial phase compensator 230 compensate the beam aberrations effectively. In such embodiments, the compensation points can be characterized only by their lateral coordinates: $r_c=(x_c, y_c)$.

As also mentioned above, in some embodiments, the aberration sensor 210 can include an optical coherence tomographic imaging system, or OCT. An OCT embodiment of the aberration sensor 210 can generate an in-depth image of the cornea 2 and its aberration-causing wrinkles. The compensation controller 220 can include an image processor to determine an aberration-optical-path-length $\Delta S$, or a corresponding aberration-phase-shift $\Delta S$ from the image generated by the OCT imaging system. In particular, from the image of the wrinkled cornea 2, the aberration-optical-path-length $\Delta S(r_a)$ can be determined as: $\Delta S(r_a)=\int \Delta n\, ds$, where the integral runs for the $\Delta(r_a)$ portion of the corneal thickness that is in excess of the average corneal thickness at the aberration point $r_a$, and the difference $\Delta n=n_c-n_{ah}$, is the difference between the index of refraction of the cornea ($n_c=1.377$) and that of the aqueous humor in the anterior chamber ($n_{ah}=1.337$). With this definition $\Delta S(r_a)$ is a measure of the aberration-optical-path-length, or aberration phase shift, caused by the aberration layer that needs to be compensated by a compensating phase $\Delta S(r_c(r_a))=-\Delta S(r_a)$, introduced at a corresponding, or mapped conjugate point $r_c=r_c(r_a)$ at the conjugate aberration surface 2B.

The design process of the compensation controller 220 can include a mapping of the $r_a$ aberration points to the $r$ conjugate compensating points to establish the $r_c=r_c(r_a)$ correspondence or mapping. This mapping can be complex, since the image of the aberration surface 2A may be magnified, demagnified, or spatially distorted by the distal optics 130 and other factors. The mapping can be carried out using a transfer matrix or a look-up table and can be determined by several means. By knowing the optical design of the surgical laser system 100, each aberration point $r_a$ at the aberration layer can be numerically ray-traced backwards, opposite to the propagation of the laser beam, to determine the corresponding compensation point $r_c=r_c(r_a)$ at the conjugate aberration surface 2B. Alternatively, the mapping or correspondence can be carried out by a calibration process. A calibration object, such as a grid pattern or an array of pin-holes can be placed at the location of the aberration layer 2A and its real image can be recorded by a camera at the location of the conjugate aberration surface 2B, thus determining the $r_c=r_c(r_a)$ mapping.

Since it is possible to compute the distortion- or aberration-compensating phase shift $\Delta S(r_c(r_a))=\Delta S(r_a)$ based on the image of the OCT embodiment of the aberration sensor 210 which is often already present in surgical laser system 100, the here-described embodiments of the laser system 100 do not require the installation of an additional wavefront analyzer, Shack-Hartmann analyzer, or other additional equipment. This can accelerate the system performance substantially and make it also simpler and cheaper.

As described above, positioning the spatial phase compensator 230 at the conjugate aberration surface 2B makes it possible that the compensation controller 220 is configured to generate the compensation-point-dependent phase compensation control signals before the proximal optics 120 and the distal optics 130 scan the laser beam in the target region, since the phase compensation control signals depend only on the compensation points $r_c$ but not on the scanning points $r_s$ and thus need not be re-calculated for every new scanning point $r_s$.

Accordingly, in some embodiments the compensation-point ($r_c$)-dependent phase compensation control signals that correspond to the aberration-compensating phase shift $\Delta S(r_c)$ can be the same for at least two different scanning points $r_s$. Also, in some embodiments the compensation-point ($r_c$)-dependent phase compensation control signals that correspond to the aberration-compensating phase shift $\Delta S(r_c)$ can be independent from a scanning point $r_s$ for an interval of the scanning point $r_s$.

Similarly, in some embodiments the spatial phase compensator 230 can alter a phase of the laser beam in a compensation-point ($r_c$)-dependent manner for at least two different scanning points $r_s$. Further, in some embodiments the spatial phase compensator 230 can alter a phase of the laser beam in a compensation-point ($r_c$)-dependent manner independent from a scanning point $r_s$ for an interval of the scanning points $r_s$.

In some embodiments of the surgical laser system 100, the aberration sensor 210 and the compensation controller 220 can be integrated into a single, integrated aberration controller.

Figure 6:
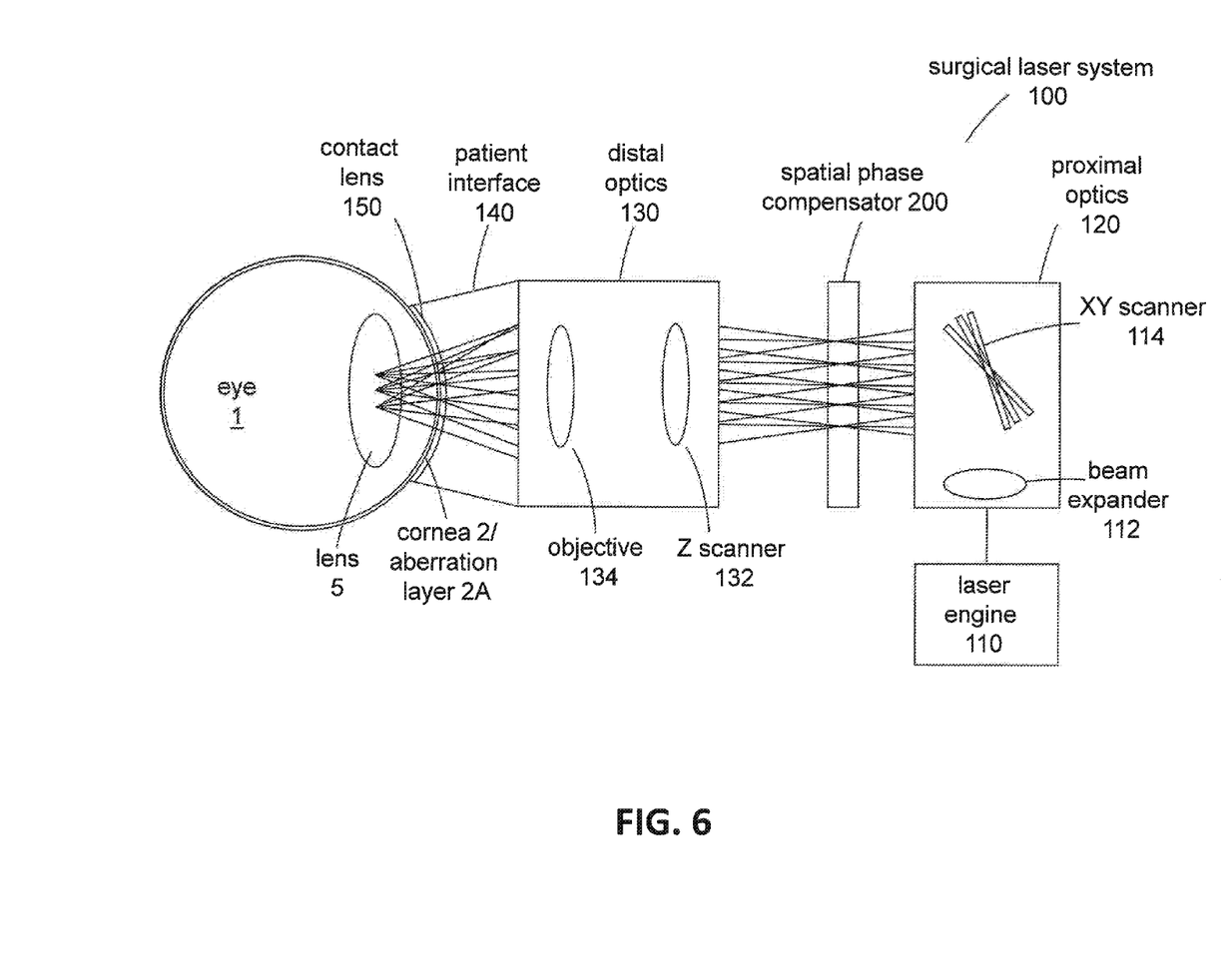
FIG. 6 illustrates an embodiment of the ophthalmic surgical laser system with a spatial phase compensator.

FIG. 6 illustrates that in some embodiments of the surgical laser system 100, the proximal optics 120 can include possibly a beam expander 112 and an XY scanner 114, whereas the distal optics 130 can include a Z scanner 132 and an objective 134. (The beams are indicated only partially for clarity.)

Alternatively, the surgical laser system 100 can include an embodiment of the proximal optics 120 that includes a beam expander 112, and the distal optics 130 includes an XY scanner, a Z scanner, and an objective.

Figure 7A:
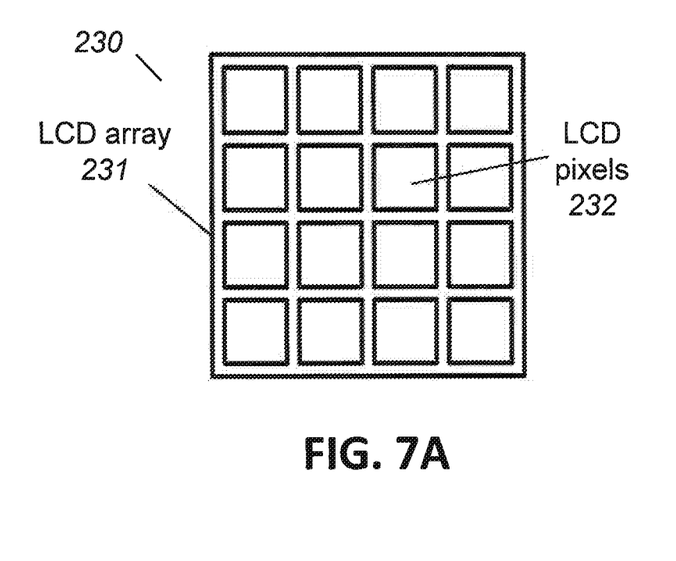
FIGS. 7A-B illustrate embodiments of spatial phase compensators.
Figure 7B:
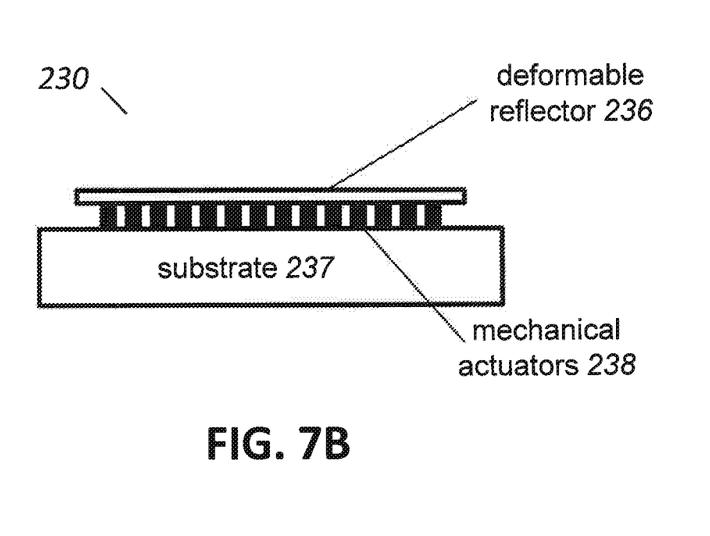

FIGS. 7A-B illustrate that the spatial phase compensator 230 can be a transmissive system, an absorptive system, or a reflective system.

FIG. 7A illustrates that in some cases the spatial phase compensator 230 can include an LCD array 231 that includes electronically controllable liquid crystal display elements or pixels 232.

FIG. 7B illustrates that in some cases the spatial phase compensator 230 can include a deformable reflector 236 that includes a substrate 237 and an array of electronically controllable mechanical actuators 238.

Many other embodiments can be included as well. For example, the spatial phase compensator 230 can include an array of electronically controllable micro-reflectors.

Finally, a method 300 of reducing aberrations in a surgical laser system may include:

(310)—generating a laser beam of laser pulses by a laser engine;

(320)—directing the laser beam to a target region by a proximal optics and a distal optics;

(330)—scanning the laser beam in the target region by the proximal optics and the distal optics through a sequence of scanning points;

(340)—sensing aberration, caused by an aberration layer, with an aberration sensor;

(350)—generating compensation-point-dependent phase compensation control signals based on the sensed aberration by a compensation controller, coupled to the aberration sensor; and (360)—altering a phase of the laser beam in a compensation-point-dependent manner to compensate the sensed aberration by a spatial phase compensator, positioned between the proximal optics and the distal optics, at a conjugate aberration surface, conjugate to the aberration layer, and coupled to the compensation controller to receive the compensation-point-dependent phase compensation control signals.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A surgical laser system, comprising:
a laser engine, configured to generate a laser beam of laser pulses;
a proximal optics and a distal optics, together configured
    to direct the laser beam to a target region within an eye, and
    to scan the laser beam in the target region through a scanning-point sequence;
an aberration sensor, configured to sense aberration by an aberration layer, wherein the aberration layer comprises a boundary of a cornea of the eye, and wherein the aberration sensor comprises an optical coherence tomographic (OCT) imaging system configured to sense aberration by generating an in-depth image of the cornea that includes the aberration layer;
a compensation controller, coupled to the aberration sensor and comprising an image processor, configured to:
    determine, from the image generated by the OCT imaging system, an aberration optical path length or aberration phase shift $\Delta S(r_a)$ for a plurality of aberration points $r_a$;
    identify, for each of the plurality of aberration points $r_a$, a corresponding conjugate compensation point $r_c$ based on a mapping which accounts for magnification, demagnification, or spatial distortion of the aberration layer,
    determine, for each conjugate compensation point $r_c$, an aberration-compensating phase shift $\Delta S(r_c(r_a)) = \Delta S(r_a)$; and
    for each compensation point $r_c$, generate a phase compensation control signal based on the determined aberration-compensating phase shift $\Delta S(r_c(r_a))$ to cause a spatial phase compensator to alter a phase of the laser beam independently at each compensation point $r_c$; and
the spatial phase compensator, positioned between the proximal optics and the distal optics, at a conjugate aberration surface, conjugate to the aberration layer, and coupled to the compensation controller, configured
    to receive the phase compensation control signal for each compensation point $r_c$, and
    to alter a phase of the laser beam independently at each compensation point $r_c$ to compensate the sensed aberration.

2. The surgical laser system of claim 1, wherein:
the distal optics includes a patient interface with a contact lens, and
the aberration layer has a fixed relationship with the contact lens.

3. The surgical laser system of claim 2, wherein:
the aberration layer tracks a distal surface of the contact lens at a distance between 0.1 mm-1 mm.

4. The surgical laser system of claim 1, wherein:
at least one of the distal optics and the proximal optics is designed so that the conjugate aberration surface is essentially flat.

5. The surgical laser system of claim 1, wherein:
the aberration sensor and the compensation controller are integrated into an aberration controller.

6. The surgical laser system of claim 1, wherein:
the compensation controller is configured to generate the phase compensation control signals before the proximal optics and the distal optics scan the laser beam in the target region.

7. The surgical laser system of claim 1, wherein:
the phase compensation control signals are the same for at least two different scanning points.

8. The surgical laser system of claim 1, wherein:
the phase compensation control signals are independent from a scanning point for an interval of the scanning points.

9. The surgical laser system of claim 1, wherein:
the spatial phase compensator is configured to alter a phase of the laser beam at a particular compensation point $r_c$ for at least two different scanning points.

10. The surgical laser system of claim 1, wherein:
the spatial phase compensator is configured to alter a phase of the laser beam at a particular compensation point $r_c$ independent from a scanning point for an interval of the scanning points.

11. The surgical laser system of claim 1, wherein:
the proximal optics comprises
an XY scanner, and
the distal optics comprises
a Z scanner, and
an objective.

12. The surgical laser system of claim 1, wherein:
the proximal optics comprises
a beam expander, and
the distal optics comprises
an XY scanner,
a Z scanner, and
an objective.

13. The surgical laser system of claim 1, the spatial phase compensator comprising:
at least one of a transmissive system, an absorptive system and a reflective system.

14. The surgical laser system of claim 13, the spatial phase compensator comprising:
an array of electronically controllable electro-optical beam modulators.

15. The surgical laser system of claim 13, the spatial phase compensator comprising:
an array of electronically controllable liquid crystal display elements.

16. The surgical laser system of claim 13, the spatial phase compensator comprising:
an array of electronically controllable micro-reflectors.

17. The surgical laser system of claim 13, the spatial phase compensator comprising:
an array of electronically controllable pixels.

18. The surgical laser system of claim 13, wherein:
the compensation controller and a scanning controller are separate.

19. A method of reducing aberrations in a surgical laser system, the method comprising:
generating, with an optical coherence tomographic (OCT) imaging system, an in-depth image of an aberration layer, the aberration layer comprising cornea of an eye;

determining, by a compensation controller coupled to the aberration sensor, an aberration optical path length or aberration phase shift $\Delta S(r_a)$ for a plurality of aberration points $r_a$ from the generated image;

identifying, by the compensation controller, for each of the plurality of aberration points $r_a$, a corresponding conjugate compensation point $r_c$ based on a mapping which accounts for magnification, demagnification, or spatial distortion of the aberration layer, determining, by the compensation controller, for each conjugate compensation point $r_c$, an aberration-compensating phase shift $\Delta S(r_c(r_a))=\Delta S(r_a)$;

generating, by the compensation controller, a phase compensation control signal for each compensation point $r_c$ based on the aberration characteristic aberration-compensating phase shift $\Delta S(r_c(r_a))$; and altering a phase of a scanned laser beam at each compensation point $r_c$ according to the phase compensation control signals to compensate the sensed aberration by a spatial phase compensator, positioned between the proximal optics and the distal optics, at a conjugate aberration surface, conjugate to the aberration layer, and coupled to the compensation controller to receive the phase compensation control signals.

* * * * *